(12) United States Patent
Shang

(10) Patent No.: US 9,561,052 B2
(45) Date of Patent: Feb. 7, 2017

(54) DISPOSABLE APPARATUS FOR FITLY CIRCUMCISING A PENIS

(76) Inventor: Jianzhong Shang, Wuhu (CN)

( * ) Notice: Subject to any disclaimer, the term of this patent is extended or adjusted under 35 U.S.C. 154(b) by 491 days.

(21) Appl. No.: 13/527,127

(22) Filed: Jun. 19, 2012

(65) Prior Publication Data

US 2012/0277759 A1 Nov. 1, 2012

Related U.S. Application Data

(63) Continuation-in-part of application No. 12/072,722, filed on Feb. 27, 2008, now abandoned.

(51) Int. Cl.
*A61F 2/16* (2006.01)
*A61B 17/326* (2006.01)

(52) U.S. Cl.
CPC .................................. *A61B 17/326* (2013.01)

(58) Field of Classification Search
CPC ................................................. A61B 17/326
USPC ........................................................ 606/118
See application file for complete search history.

(56) References Cited

U.S. PATENT DOCUMENTS

| | | | | |
|---|---|---|---|---|
| 5,072,720 A | * | 12/1991 | Francis et al. | 600/186 |
| 5,269,788 A | * | 12/1993 | Nelson, III | 606/118 |
| 2011/0098718 A1 | * | 4/2011 | Shang | A61B 17/326 |
| | | | | 606/118 |

FOREIGN PATENT DOCUMENTS

| CN | 201710425 | * | 1/2011 |
|---|---|---|---|
| CN | 102068297 | * | 5/2011 |
| WO | WO 2005/039424 | * | 5/2005 |

OTHER PUBLICATIONS http://www.thefreedictionary.com/blade, as accessed on Aug. 21, 2015.*

* cited by examiner

*Primary Examiner* — Todd J Scherbel
(74) *Attorney, Agent, or Firm* — Gokalp Bayramoglu

(57) ABSTRACT

A disposable circumcision apparatus, comprising, a fixture device comprising a surrounding wall, the surrounding wall comprising an opening, a blade formed along an interior surface of the surrounding wall, the blade comprising a first blade mating portion and a second blade mating portion that mate with each other when the fixture device is in a closed position, the blade further comprising a blade interior circumferential edge, a cushion ring for being positioned against the blade further comprising a groove formed along a blade interior circumferential edge, means for maintaining the fixture device in a closed position, and a balanus ferrule for placement within the cushion ring and fixture device.

18 Claims, 20 Drawing Sheets

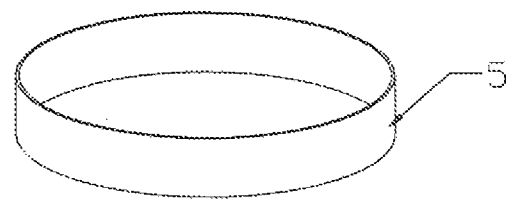
FIG. 6
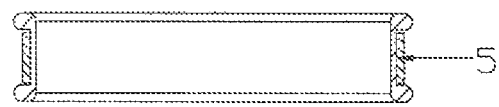
FIG. 7
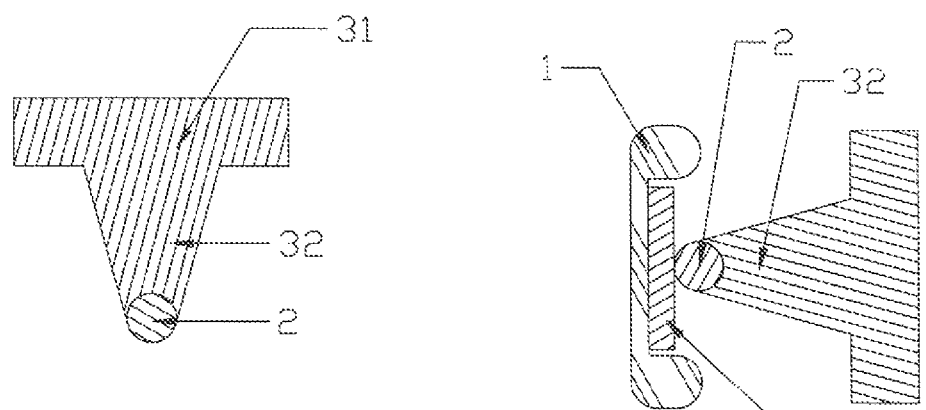
FIG. 8
FIG. 9

DISPOSABLE APPARATUS FOR FITLY CIRCUMCISING A PENIS

CLAIM OF PRIORITY

This application is a continuation-in-part of, and claims priority to, U.S. patent application Ser. No. 12/072,722, filed on Feb. 27, 2008, owned by the inventor of the present, the entire contents of which are incorporated by reference herein.

FIELD OF THE INVENTION

The invention relates to a type of apparatus for fitly circumcising a penis, especially a type of circumcision apparatus that prevents a fixture device from opening during a circumcision procedure.

BACKGROUND

The effect of male circumcision has been widely recognized in reducing the transmission of HIV. Mr. Jianzhong Shang has previously invented a disposable circumcision apparatus that utilizes upper and lower blades that join to form a circular clamp, the blades staggered from one another, so as to minimize pain resulting from skin clamping during the procedure. This technique has been improved over the years to further ensure the convenience, safety, and effectiveness of this operation on a wide range of patients. This circumcision apparatus is the present standard in circumcision surgery.

The disposable circumcision device mentioned above comprises a fixture device (exterior ring) and balanus ferrule (interior ring), which are made of hard, non-toxic medical plastics. A patient may experience pain and discomfort during surgery as a result of the hard, circular clamp and balanus ferrule directly contacting the prepuce.

One problem with the prior art circumcision device mentioned above is the possibility of dropping the device during the procedure, which may directly lead to bleeding. Additionally, a patient may be fearful of such an accidental during the circumcision procedure and cause unnecessary mental anguish prior to the procedure. Some have attempted to reduce the chances of dropping a circumcision apparatus during the procedure by using scalariform detent blocks at each end of the circumcision apparatus, so as to prevent the accidental opening of the fixture device that may lead to dropping the entire apparatus. The current Shanghuan Brand circumcision apparatus uses this technique.

It would be desirable to avoid the pain and discomfort associated with the prepuce being in direct contact with the circular blades of the fixture device and balanus ferrule.

SUMMARY

A disposable circumcision apparatus, comprising a fixture device comprising a surrounding wall, the surrounding wall comprising an opening, a blade formed along an interior surface of the surrounding wall, the blade comprising a first blade mating portion and a second blade mating portion that mate with each other when the fixture device is in a closed position, the blade further comprising a blade interior circumferential edge, a cushion ring for being positioned against the blade further comprising a groove formed along a blade interior circumferential edge, means for maintaining the fixture device in a closed position, and a balanus ferrule for placement within the cushion ring and fixture device.

The beneficial effects of the invention are as follows:

1. An interior circumferential edge of each blade has a groove for retaining a cushion ring, such as a non-toxic medical silica-gel cushion ring, which clamps directly on the prepuce. A soft elastic pad is also provided on the surface of a balanus ferrule. Therefore, both the outer and inner surfaces of prepuce touch a soft material, providing some space for expansion and effectively alleviating the pain and discomfort caused by prepuce irritation against the prior art hard surfaces of the half-ring and balanus ferrule.
2. The first blade mating portion and the second blade mating portion are proceeded at the open end of the blade, respectively. These portions of the blade are designed to slide over each other, or overlap, to form a complete blade structure (e.g., ring) as the fixture device is placed into a closed position. The first and second blade better facilitate clamping of the fixture device around the foreskin of the penis during surgery. When in use, the cushion ring will neither be obstructed at the fixture device opening due to wrinkling nor clamp the prepuce during the procedure when the upper and second blade come in contact with each other.
3. A micro mechanism preventing skin adhesion may be provided for both the cushion ring and the elastic pad, so as to reduce the possibility of skin adhesion of the prepuce, reducing pain associated with the circumcision apparatus removal process.
4. A hook and a linear groove may be provided on each side of a buckling device located on each open end of the fixture device, and a protective cover may be provided over the buckling device, minimizing the risk of the buckling device opening due to, for example, a penile erection.
5. The cross section of both the fixture device and balanus ferrule may form an elliptic or obliquely elliptic structure, which may more closely resemble the cross section of an actual penis, especially the shape of the coronal sulcus. The pain resulting from irritating the frenulum during an erection is further reduced.
6. The fixture device may comprise a one-section, two-section, or three-section ring-shaped apparatus. The one-section fixture device may be made exclusively of soft materials, has an adjustable opening and is simple and convenient. The two-section fixture is typically made of hard, non-toxic medical plastics that are rotatably joined together at one end, forming an adjustable opening at the other. In this embodiment, the fixture device is rigid, ensuring the structural integrity of the circumcision apparatus. Additionally, this embodiment allows for a large opening formed at the "open" ends of the two semi-ferrules via the hinge structure formed by at the two, opposing ends of the semi-ferrules. During surgery, the connecting ends are typically located above of the scrotum, causing friction between the hinge and the scrotum, thereby causing patient discomfort. The three-section design may alleviate this problem, because two pivot points are staggered from each other so that contact with the scrotum is reduced or completely eliminated.
7. A notch for receiving the frenulum may be provided within the balanus ferrule, shaped to correspond with the penis structure and preventing pressure on the frenulum.

BRIEF DESCRIPTION OF THE DRAWINGS

FIG. 6 illustrates a circular elastic pad used in one embodiment;

FIG. 7 illustrates a cross-section of the balanus ferrule used with the circular elastic pad;

FIG. 8 illustrates a cross-section of the cushion ring as it is seated into the half-ring groove of the fixture device;

FIG. 9 illustrates a cross-section of the fixture device, cushion ring, balanus ferrule, and circular elastic pad in one embodiment as they are interconnected with each other;

DETAILED DESCRIPTION OF THE PREFERRED EMBODIMENTS OF THE INVENTION

Figure 1A:
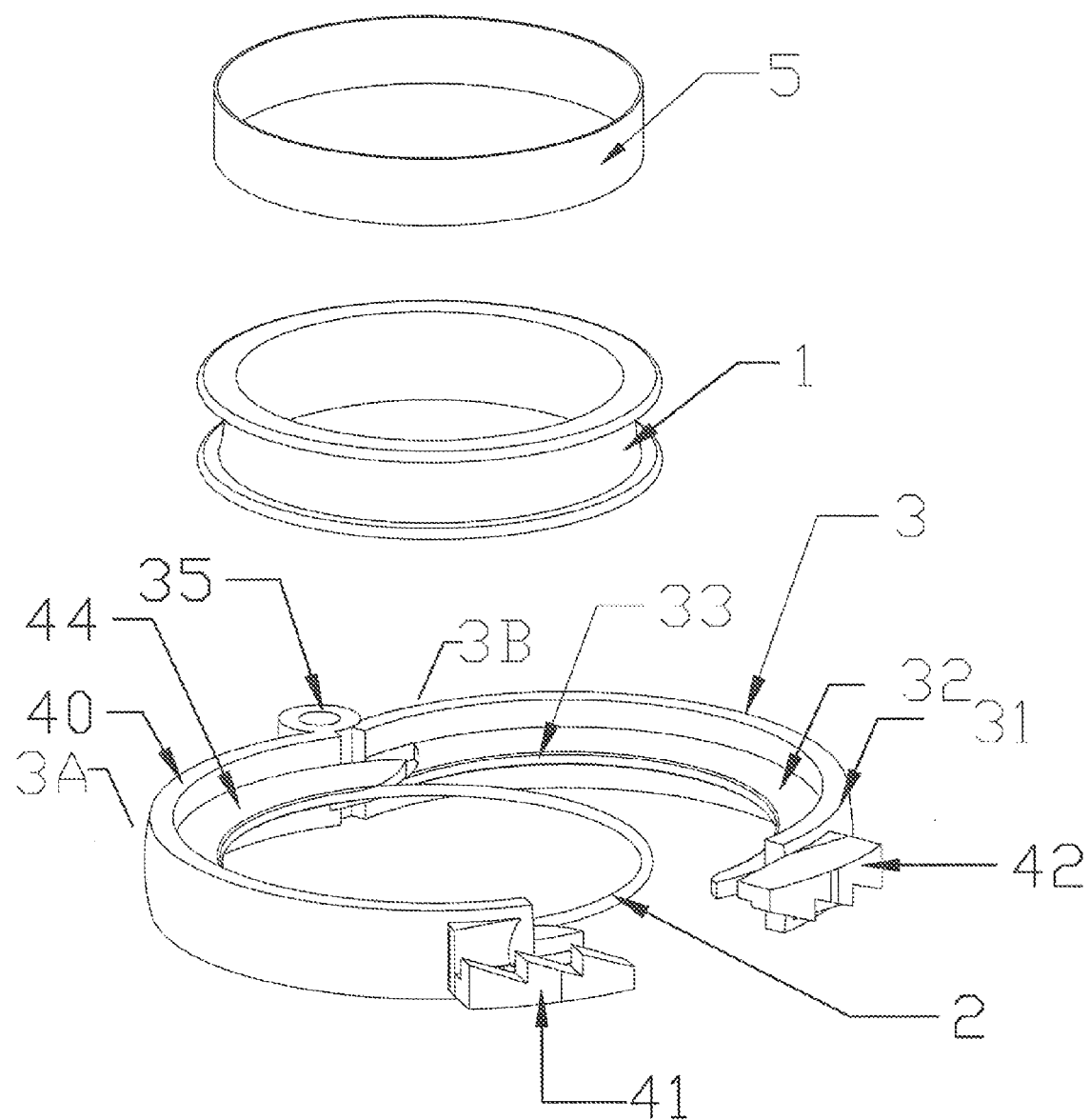
FIG. 1A is an exploded view of an apparatus for circumcising a penis, comprising a fixture device, balanus ferrule, cushion ring, and circular elastic pad.

As shown in FIG. 1A, a disposable apparatus for circumcising a penis (circumcision apparatus) comprises fixture device 3, balanus ferrule 1, and optional elastic pad 5, the fixture device 3 comprising a right surrounding wall 31, left surrounding wall 40, right blade 32, and left blade 44. The fixture device 3 forms an opening through which a penis can be easily placed during a circumcision procedure. The fixture device comprises at least one hinged connection, allowing the fixture device to close around the penis, where it may then be secured by a buckling device 4 incorporated into the fixture device structure.

In order to avoid the pain resulting from clamping fixture device 3 and balanus ferrule 1 onto the prepuce, the present invention utilizes a cushion ring 2 that engages a groove 33 formed on an interior circumference of the blade (which is closest to the balanus ferrule 1 during a circumcision procedure).

Figure 2C:
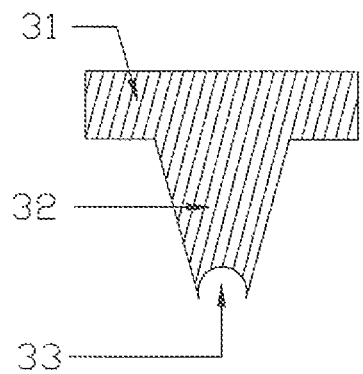
FIGS. 2C, 2D, and 2E illustrate vertical cross-sections of three different embodiments of the fixture device shown in FIG. 1A, respectively.
Figure 2D:
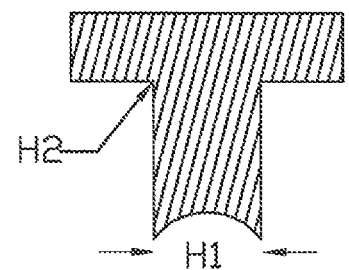
Figure 2E:
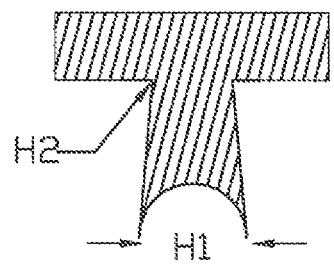
Figure 3A:
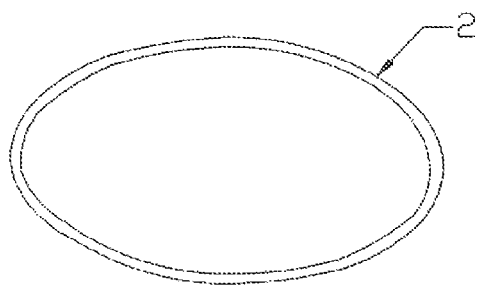
FIGS. 3A, 3B, and 3C are illustrations showing various views of the cushion ring shown in FIG. 1A in an embodiment where cushion ring is circular.

According to a first embodiment, the groove 33 is formed on the inside circumference of the blade. As shown in FIG. 2C, in one embodiment, the cross-section of groove 33 is of semi-circular shape. As shown in FIGS. 3A, 3B, and 3C, the cross-section of the cushion ring interconnected with groove 33 is of circular shape, and the diameter thereof is less than or equal to that of the circular groove. The circumference of the cushion ring is about equal to that of the blade edge when the fixture device is closed. The cushion ring is typically held in place by the geometry of the groove and ring. Of course, the groove 33 may, alternatively, comprise an arc, semi-elliptic, square, or triangular shape, any of which can be made to accept the cushion ring 2. As shown in FIGS. 2D and 2E, in order to save materials, the inner side of the blade (H1) can be equal to or thicker than that of outer side of the blade (H2).

Figure 1B:
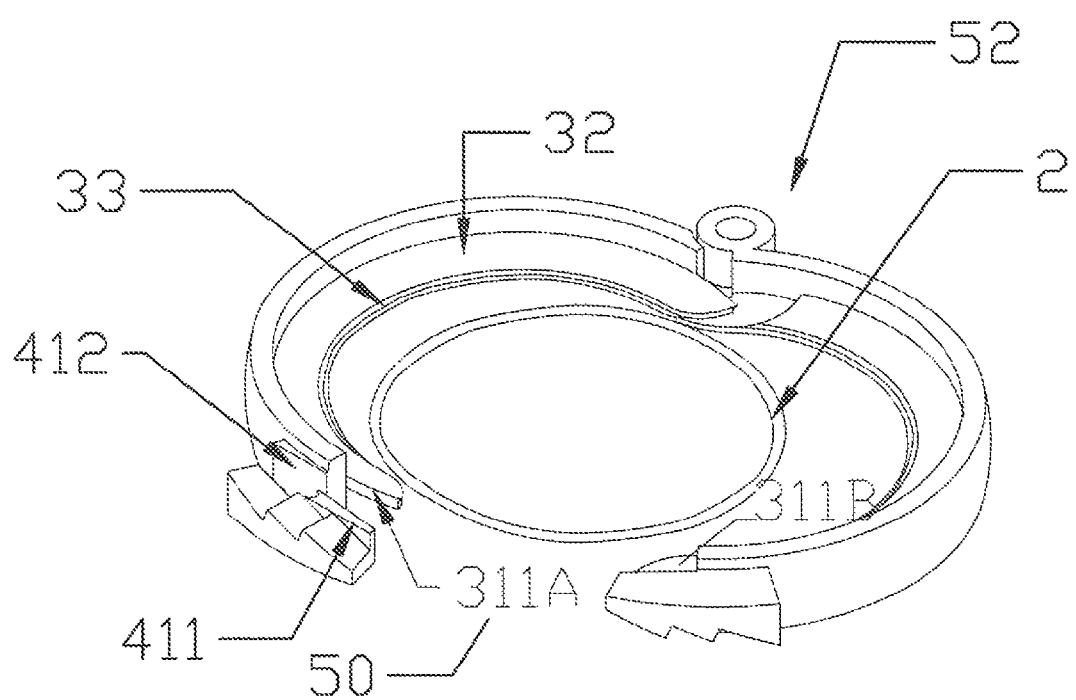
FIG. 1B illustrates the fixture device and cushion ring of FIG. 1A interconnected with one another.
Figure 2A:
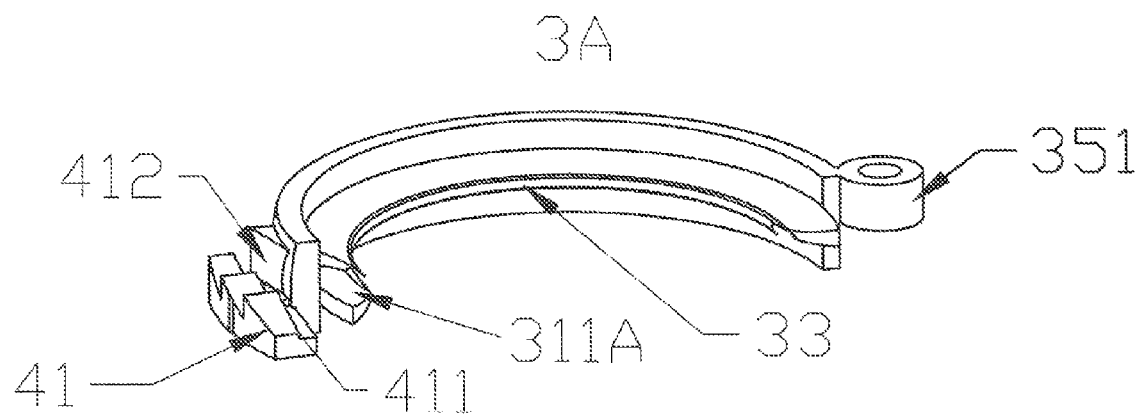
FIGS. 2A and 2B illustrate left and right semi-ferrules, respectively, of the fixture device shown in FIG. 1A.
Figure 2B:
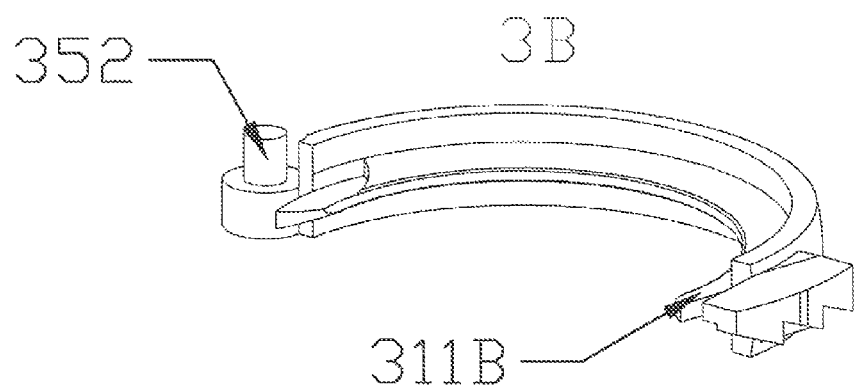
Figure 2F:
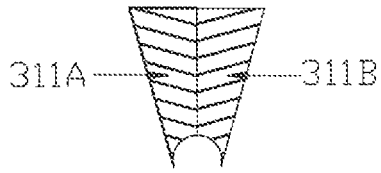
FIGS. 2F, 2G, and 2H illustrate first and second mating half-ring portions of three different embodiments of the fixture device shown in FIGS. 2C, 2D, and 2E, respectively.
Figure 2G:
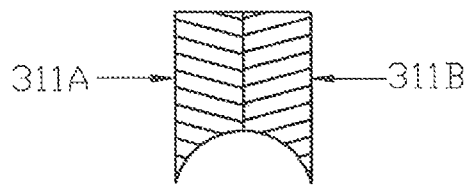
Figure 2H:
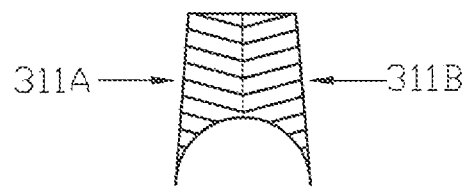

As shown in FIG. 1B, FIG. 2A, and FIG. 2B, the blade of the left semi-ferrule 3A comprises a first blade mating portion 311A and the blade of the right semi-ferrule 3B comprises a second blade mating portion 311B at the open end of the blade, respectively. These portions of the blade are designed to slide over each other, or overlap, to form a complete blade structure (e.g., ring) as the fixture device is placed into a closed position. Thus, the thickness of both the first and second blade mating portions are thinner than the majority of the blade structures. In one embodiment, the mating portions comprise rounded edges. FIGS. 2F, 2G, and 2H illustrate three embodiments of the first and second mating blade portions when the fixture device is in a closed position. The groove formed on the interior circumference of the blade extends into the mating portions, however the cross section of the groove in the mating portions are half of what they are in the majority of the blade. Thus, when the fixture device is placed into a closed position, the groove that is formed on the majority of the blade continues uninterrupted in the mating portions, as the groove is completed as the mating portions align with one another.

As shown in FIGS. 1A, 1B 2A and 2B, the fixture device 3 comprises a two-section design, each section having an open end 50 and a connecting end 52. In this embodiment, fixture device 3 comprises the left semi-ferrule 3A and right semi-ferrule 3B. The connecting ends are rotatably connected to one another via a hinged connection 35 (shown in FIG. 1A), which comprises connecting linear groove 351 on one semi-ferrule and connecting rod shaft 352 on the other semi-ferrule (shown in FIG. 2A and FIG. 2B). The open end 50 on left semi-ferrule 3A comprises a means for mating with a reciprocal means located on the open end of the right semi-ferrule 3B. In this way, the fixture device can be easily applied and removed during circumcision surgery. Furthermore, adequate rigidity of the blade may be achieved by using hard materials. The design of the first and second mating blade portions effectively prevent the blade from pinching the penis when using the circumcision device during surgery. Additionally, the structure effectively guides the cushion ring into the blade groove 33. Thus, the cushion ring fits easily within the complete groove formed as the fixture device is closed, and is not clamped or pinched at the open or connecting ends.

Figure 2I:
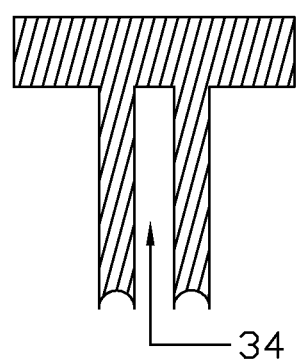
FIGS. 2I and 2J illustrate a cross-section of two embodiments of the fixture device of FIG. 1A, each having two blade.
Figure 2J:
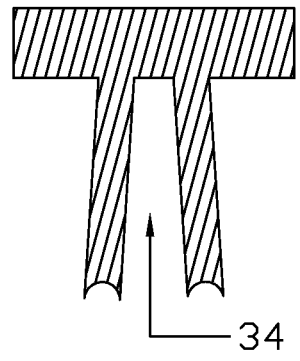
Figure 2K:
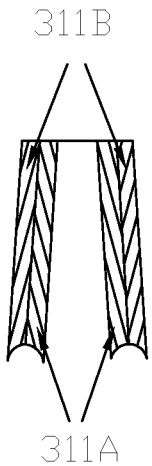
FIG. 2K is an illustration of first and second mating blade portions for the structure of FIG. 2J.

In another embodiment, each semi-ferrule may comprise two or more blade. As shown in FIGS. 2I and 2J (depicting a cross section of either right blade 32 or left blade 44), each semi-ferrule comprises two blade, each comprising an inner circumference having a groove to accommodate a cushion ring, while a cavity 34 is formed between the two blade for containing cotton wool or ointment. As shown in FIG. 2K illustrating the mating portions for open or connecting end for both blade, the left semi-ferrule comprises two mating blade portions 311A (inner), and the right semi-ferrule comprises two mating blade portions 311B (outer). As the circumcision device is closed, the two mating blade portions 311B overlap the two mating blade portions 311A to form a complete ring structure.

Figure 3D:
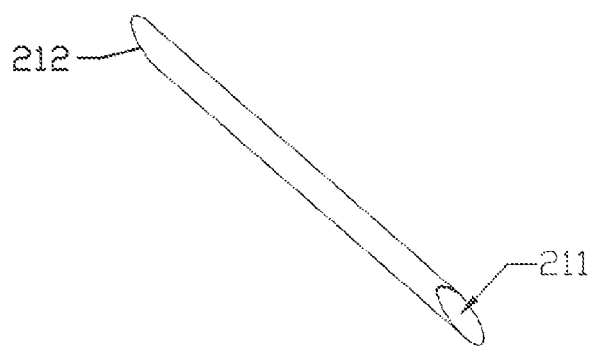
FIG. 3D is an illustration of a linear cushion ring used in one embodiment.
Figure 3C:
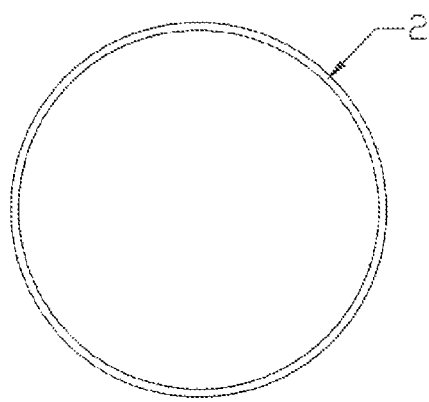
Figure 3B:

In an alternative embodiment, the cushion ring 2 may comprise the linear structure shown in FIG. 3D, which can be directly inserted into groove 33 of the blade. In this embodiment, each end 211 and 212 of the linear structure are cut off at an angle, such as 45 degrees, and these ends lie on top of the first blade mating portion and second blade mating portion, respectively, after it has been inserted into the groove. When the fixture device is closed, the linear cushion ring forms a full ring shape.

Figure 4A:
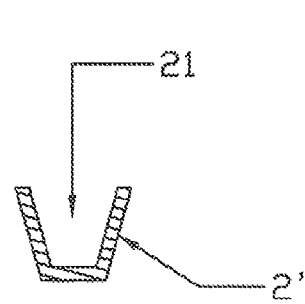
FIGS. 4A, 4B, 4C, 4D, 4E, 4F, 4G, and 4H illustrate various embodiments of how the cushion ring and blade shown in FIG. 1 may be joined.
Figure 4B:
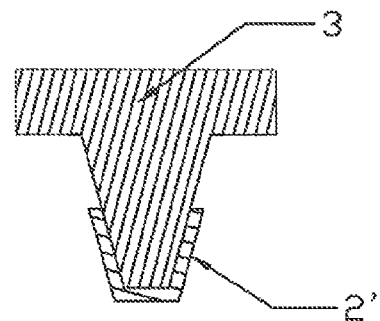
Figure 4C:
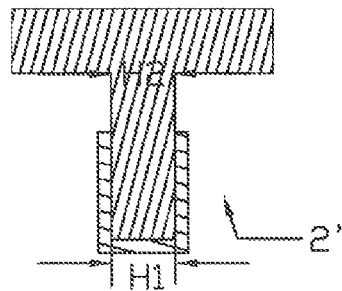
Figure 4D:
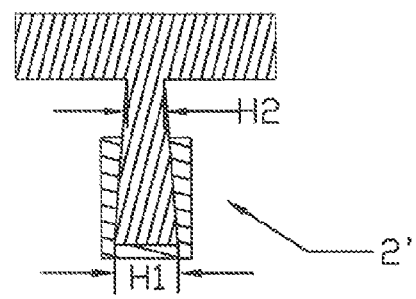
Figure 4E:
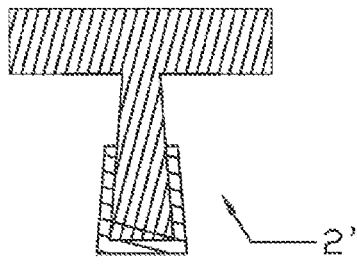
Figure 4F:
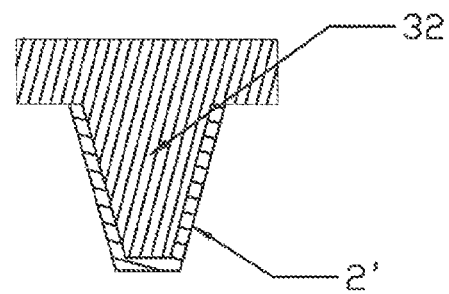
Figure 4G:
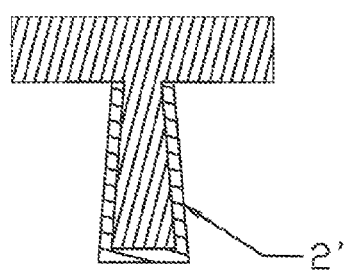
Figure 4H:
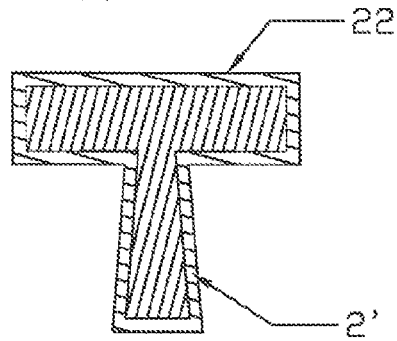

Another embodiment of the cushion ring is illustrated in FIGS. 4A and 4B. In this embodiment, the cushion ring comprises a groove 21 that overlaps the inner circumference of one or both blade. As shown in FIGS. 4F and 4G, groove 21 may alternatively overlap a portion of or an entire blade, as shown in FIG. 4H.

Traditionally, the thickness of the inner circumference of a blade (H1) is thinner than the outer circumference (H2) thickness. Alternatively, the width (H1) can be equal to or larger than H2. This design can reduce the amount of materials needed to manufacture the blade/cushion ring. Another advantage is that it may be desirable for the cushion ring 2 to be attached to the blade. FIG. 4C illustrates that width H1 is equal to width H2, while FIGS. 4D and 4E illustrate that width H1 is greater than width H2. The method in which H1 is greater than or equal to H2 is desirable so that the cushion ring 2 may be steadily affixed to the blade.

In one embodiment, the cushion ring 2 is manufactured from medical non-toxic silica-gel and may be directly adhered to the blade inner circumference. In other embodiments, the cushion ring 2 may be manufactured from virtually any combination of plastics and silica-gel. In yet sill other embodiments, the blade are manufactured from a relatively hard material, such as plastic, while the cushion ring is manufactured with a less-hard substance, such as silica-gel, so that the cushion ring fits adheres to the groove by virtue of an integral formation between the plastic and the silica-gel. Furthermore, the surrounding walls 31 and 40 may be coated with a silica-gel layer 22 that adheres to the surrounding walls 31 and 40 (i.e., fixture device) through a single integral formation between plastics and silica-gel. In one embodiment, the entire fixture device is coated with a silica-gel layer, enabling the penis to directly contact this soft surface, thereby effectively increasing the patient's comfort.

Figure 5A:
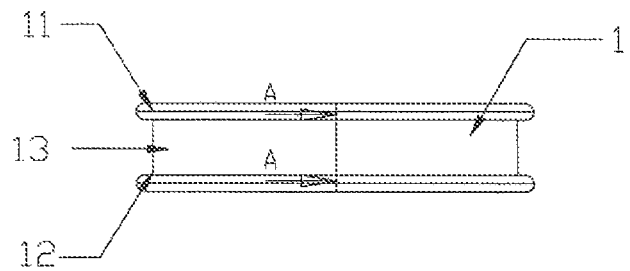
FIGS. 5A, 5B, and 5C illustrate three different views of the balanus ferrule of FIG. 1A.
Figure 5B:
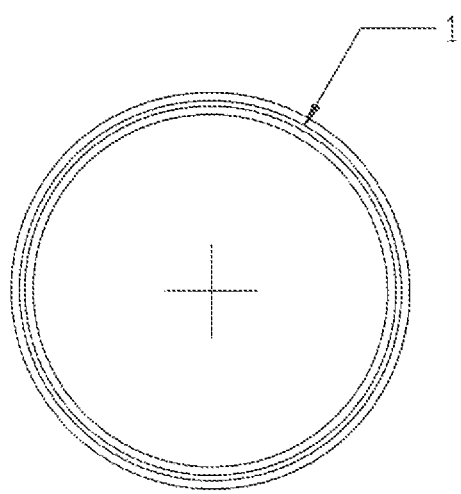
Figure 5C:

FIGS. 5A, 5B, and 5C illustrate three views of balanus ferrule 1 shown in FIG. 1A. A first rim 11 and a second rim 12 create a circular cavity 13 between the first rim 11 and the second rim 12. As shown in FIG. 6, a circular elastic pad 5 comprises a ring made of an elastic material, such as rubber or other stretchable synthetic material. As shown in FIG. 7, when in use, the elastic pad 5 is stretched over one of the rims (either rim 11 or rim 12) of the balanus ferrule 1, where it then fits snugly around the circular cavity.

Figure 10:
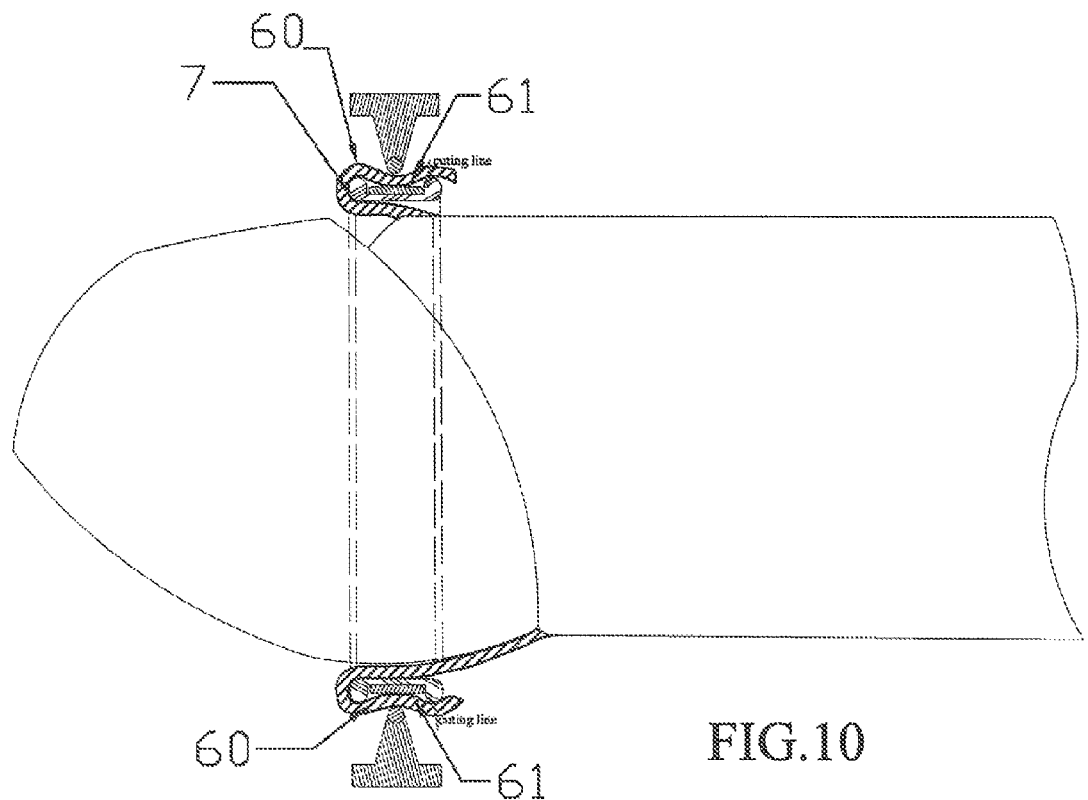
FIG. 10 illustrates one embodiment of an apparatus for circumcising a penis at it is being used during a circumcision procedure.

FIG. 8 illustrates a cross section of one of the blade and cushion ring inserted into a groove formed along an interior circumference of the blade. FIG. 9 illustrates a cross section of the blade/ring combination of FIG. 8 in contact with a cross section of the elastic pad 5 placed around the balanus ferrule 1. During a circumcision operation, a penis is placed through the balanus ferrule 1 having the circular elastic pad 5 in place over its circular cavity. Next, the prepuce 7 is unfurled to cover the balanus ferrule 1 with the unfurled portion 60 of the prepuce (shown in FIG. 10) extending from the ferrule. Then, the circular cushion ring 2 is placed around the exterior surface of the prepuce over the circular cavity 13/elastic pad 5. Next, the fixture device 3, in an open position, is placed around the cushion ring 2, aligning the groove in each blade with the cushion ring 2. Finally, the fixing device is closed by bringing the two open ends 50 of each semi-ferrule together and locking the fixing device in a closed position using the buckling device. The result, shown in a cross-sectional view, is shown in FIG. 10. At this point in the procedure, a scalpel is typical used to cut the one part of the prepuce (you can see the cutting line in FIG. 10). then after 10 to 7 days when the apparatus is on the body, the abundant prepuce 61 (the part between the cutting line and the cushion ring meets the prepuce) of the patients naturally falls off due to avascular necrosis. After removing the circumcision apparatus the cut part is very natural and smooth compared to healing after laser surgery.

Using this technique, the first and second mating blade portions can effectively prevent the skin on the penis from being pinched at the open and connecting ends of the fixture device and, additionally, the circular cushion ring is easily guided into the blade groove. Both the circular cushion ring and surrounding elastic pad are typically made of soft, non-toxic medical silica-gel, providing a certain degree of expansion and effectively minimizing the pain and discomfort normally associated with circumcision surgery.

Figure 1C:
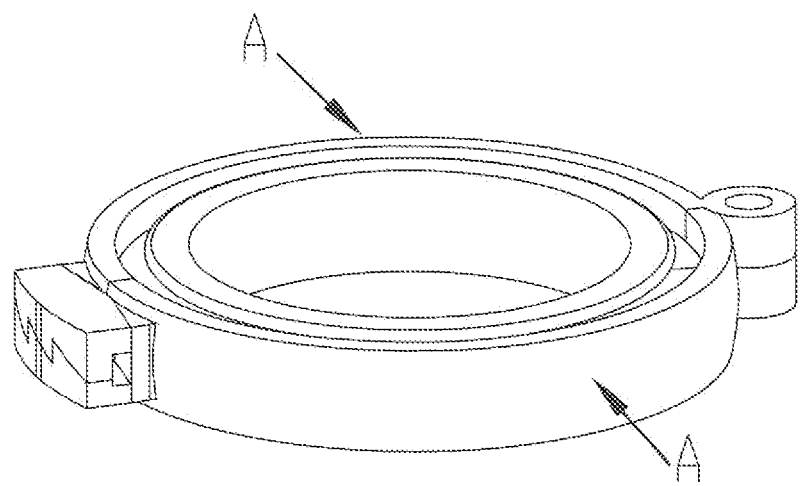
FIG. 1C is a perspective view of the apparatus of FIG. 1A in a closed position.
Figure 1D:
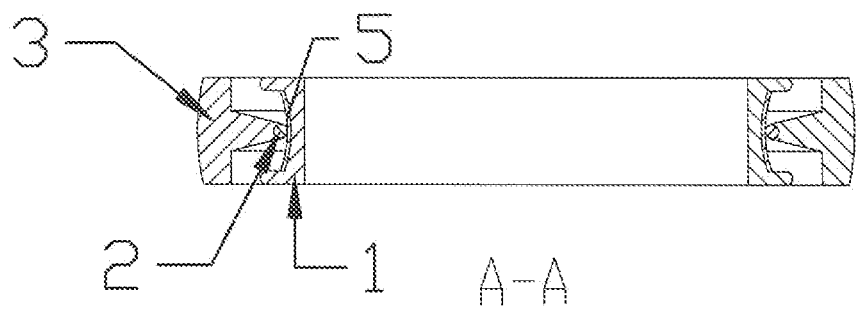
FIG. 1D illustrates cross-section A-A shown in FIG. 1C.

Turning back to FIG. 1C, the outer circumference of the surrounding walls 31 and 40 of the fixture device comprises a beautiful arc shape. As show in 1D, the exterior circumference of the balanus ferrule comprises a curved profile which can prevent the blade sliding from the middle to either rim of the balanus ferrule.

Figure 11A:
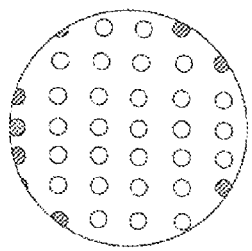
FIGS. 11A, 11B, and 11C illustrate three embodiments of micro mechanisms that prevent skin adhesion on the cushion ring and circular elastic pad.
Figure 11B:
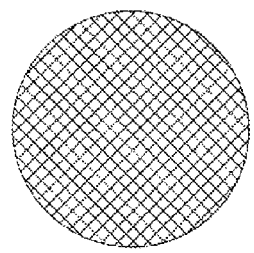
Figure 11C:
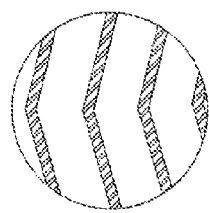

In order to prevent skin adhesion during removal of the apparatus from the penis after surgery, a micro mechanism that prevents skin adhesion may be provided on the surface of either the circular cushion ring 2, circular elastic pad 5, or both. The micro mechanism may comprise depressions or raised portions, such as the sinking and/or bulging dots shown in FIG. 11A, the crossed bulging and/or sinking streaks shown in FIG. 11B, or the grooves and/or protrusions shown in FIG. 11C. Due to the existence of the micro mechanisms, removal of the circumcision apparatus reduces the occurrence of skin adhesion, making the process of removing the circumcision apparatus easier.

Figure 12A:
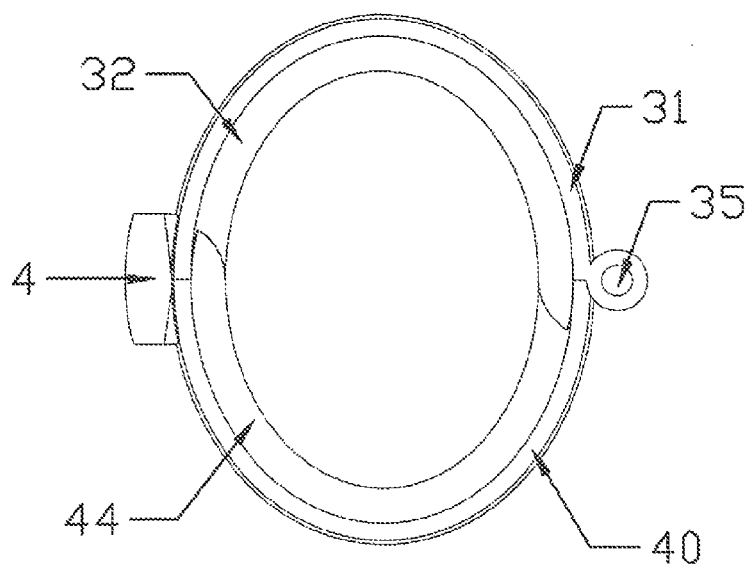
FIGS. 12A and 12B illustrate various views of the fixture device in an embodiment where the fixture device is elliptical in nature.
Figure 12B:
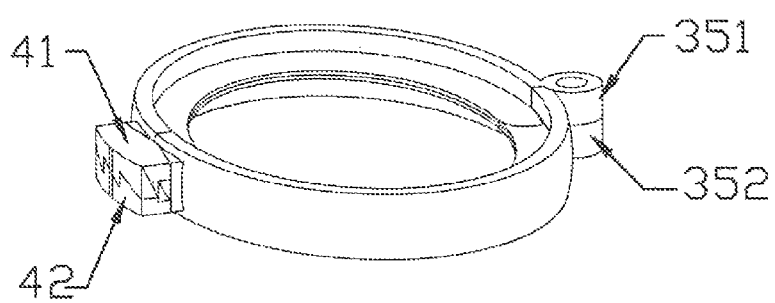
Figure 12C:
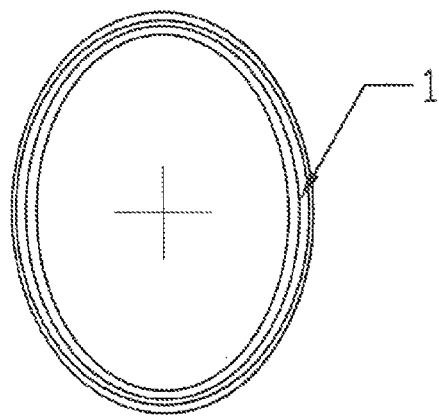
FIG. 12C illustrates one embodiment of the balanus ferrule, shown as an elliptical structure.
Figure 12D:
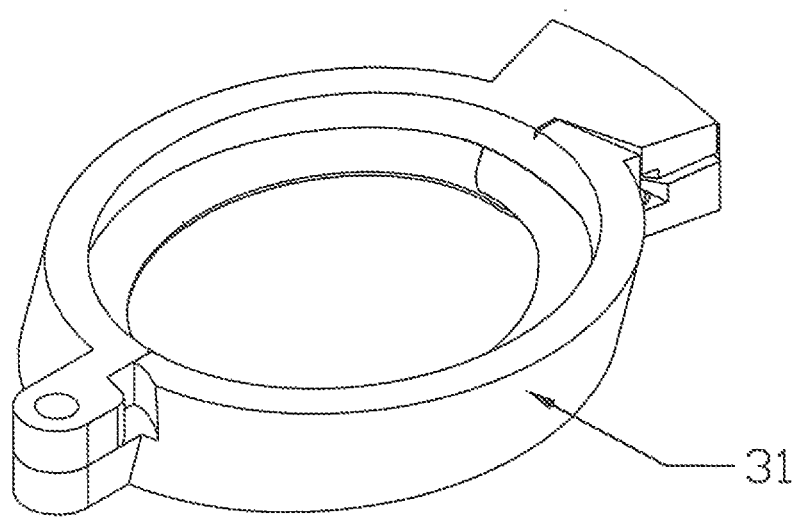
FIG. 12D illustrate another embodiment of the fixture device in an embodiment where the fixture device is elliptical and oblique.
Figure 13A:
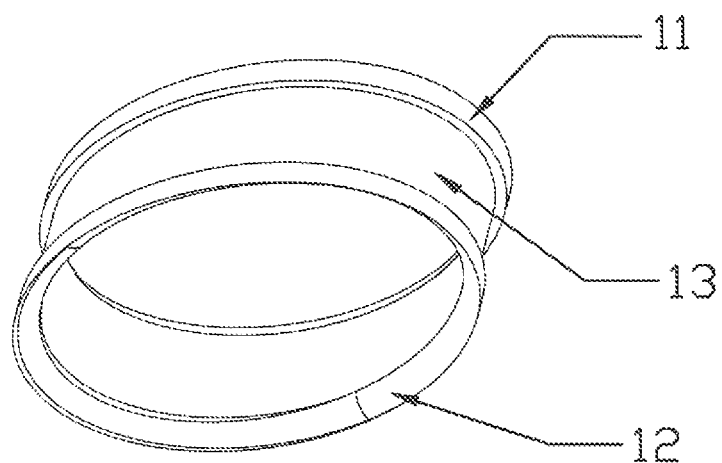
FIGS. 13A and 13B illustrate another embodiment of the balanus ferrule, shown as an elliptical and oblique structure.
Figure 13B:
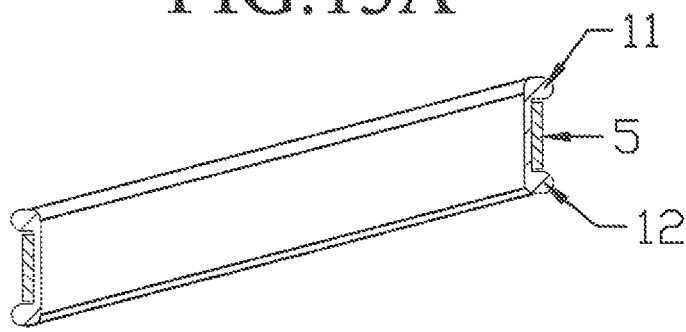
Figure 14:
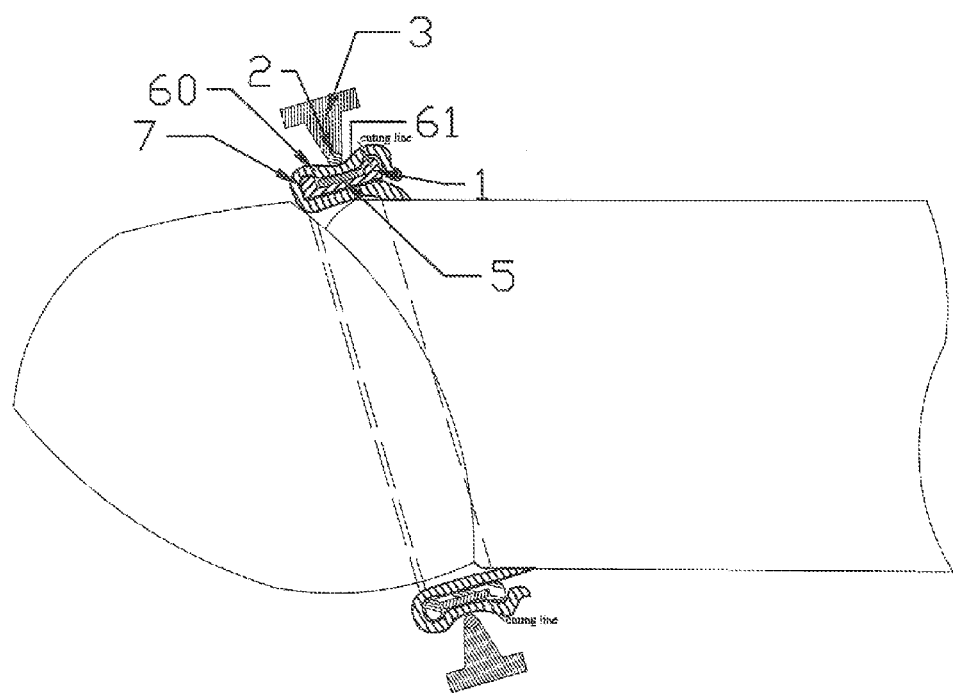
FIG. 14 is an illustration of the elliptical and oblique embodiment of the apparatus for circumcision as shown in FIGS. 12D, 13A, and 13B as it is used during circumcision surgery.

In an embodiment shown in FIGS. 12A, 12B and 12C, the fixture device 3 and balanus ferrule 1 comprise an elliptic structure. This structure may more closely resemble the cross section of an actual penis, especially the shape of the coronal sulcus. As shown in FIGS. 12D, 13A and 13B, the fixture device and the balanus ferrule are elliptical and oblique. As shown in FIG. 14, the circumcision apparatus closely matches the oblique shape of coronal sulcus, providing more comfort to the patient and ease of operation for the surgeon.

Figure 15:
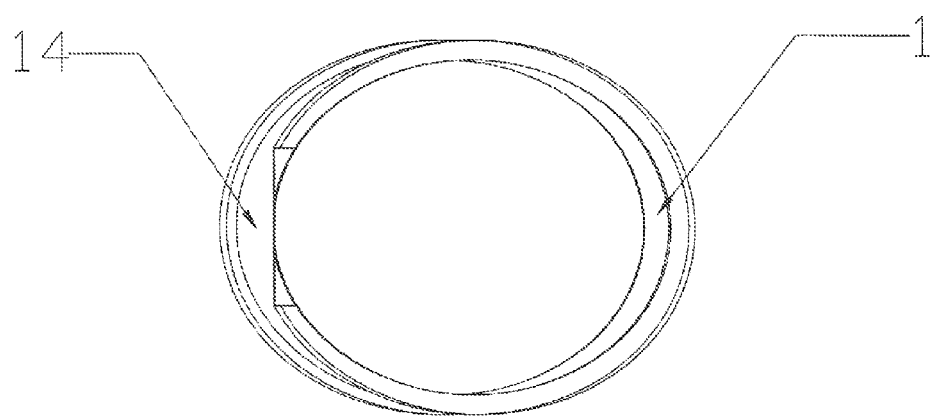
FIG. 15 illustrates a balanus ferrule in one embodiment, comprising a notch for containing the frenulum of prepuce.

As shown in FIG. 15, a notch 14 is formed for accommodating the frenulum of prepuce is provided at one side of the first and second edges of the balanus ferrule 1. While in use, the balanus ferrule may be rotated so that notch 14 accommodates the frenulum of prepuce. The notch 14 advantageously protects the frenulum and allows the circumcision device to more closely fit a human penis. Thus, the pain resulting from chaffing of the frenulum during a nocturnal erection may be reduced, thus increasing patient comfort.

Figure 16:
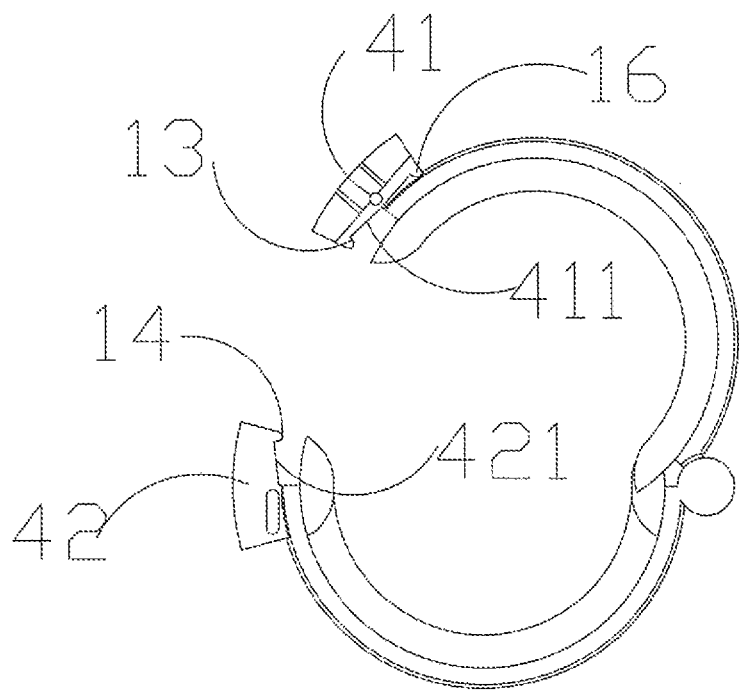
FIGS. 16 and 17 are illustrations of the fixture device in an embodiment where the fixture device comprises a hook and a linear groove.
Figure 17:
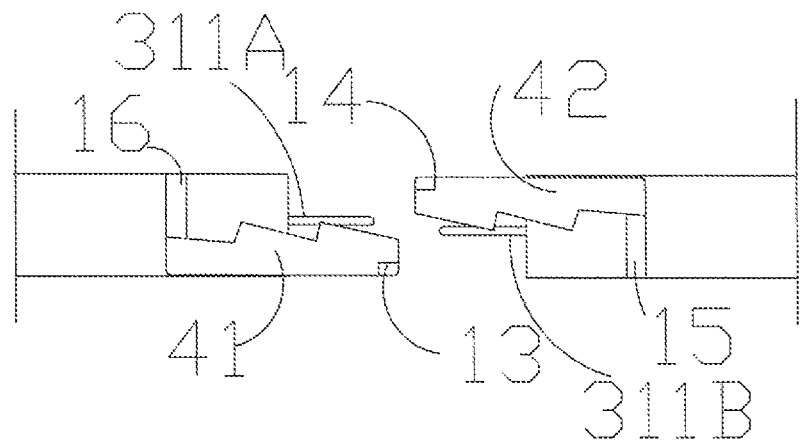

The fixture device 3 is closed (only closed not opened to avoid reuse of the apparatus) by the use of a buckling device 4, as shown in FIG. 1A and other figures. The buckling device 4 may comprise any number of structures known in the art, such as a screw located on an open end of one of the semi-ferrules and a threaded linear groove at the other open end on the other semi-ferrule that comprise fixture device 3. In another embodiment, the buckling device 4 comprises the detent block structure shown in FIGS. 16, 17, and 18A-18D. As shown in FIG. 17, the buckling device comprises an upper scalariform detent block 41 and a lower scalariform detent block 42 that are arranged in a "staggered" formation. The first mating blade portion 311A lies in a plane slightly above the lower scalariform detent block 41 and the second mating blade portion 311B lies in a plane slightly under the upper scalariform detent block 42, creating a fixture device that is self-contained and capable of being opened and closed using the buckling device.

In order to further avoid accidental opening of the buckling device, the aforesaid upper scalariform detent block 41 and lower scalariform detent block 42 may comprise a hook and linear groove that corresponds with each other. As shown in FIGS. 16, 17, and 18A-18D, in one embodiment, an upper hook 13 may be provide at the outer end of upper scalariform detent block 41 and a lower linear groove 16 (it is same to the upper linear groove 15 which clearly shown in FIG. 18A) is provided at the inner end of the upper scalariform detent block 41, while a lower hook 14 is provide at the outer end of lower scalariform detent block 42 and an upper linear groove 15 is provided at the inner end of the lower scalariform detent block 42. To close the fixture device, the upper hook 13 interacts with the upper linear groove 15, while the lower hook 14 interacts with the lower linear groove 16. When the an upper scalariform detent block 41 and a lower scalariform detent block 42 are engaged with each other, the hook and linear groove further assures that the fixture device will remain closed.

In view of the interaction between the hooks and linear grooves in the above-described embodiment, the inner sides of the upper scalariform detent block 41 and lower scalariform detent block 42 may comprise incline surfaces, and incline projecting portions, located on the surrounding walls, the incline projecting portions substantially matching the incline surfaces. This feature is shown in FIG. 2a, FIG. 16 and FIG. 18, illustrating a first incline surface 411 and a first incline projecting portion 412 on the upper scalariform detent block 41 and a second incline surface 421 (FIG. 16) and second incline projecting portion 422 (FIG. 18A) on the lower scalariform detent block 42. The upper hook 13 is provided at the outer side of the first incline surface 411 and the lower hook 14 is provided at the outer side of second incline surface 421. The lower linear groove 16 is provided at the end of the first incline projecting portion 412 (on the opposite of the upper hook 13) and the upper linear groove 15 at the end of the second incline projecting portion 422 (on the opposite of the lower hook 14). There may be holes which substantially matching the hooks. The hooks and linear grooves or holes further substantially match with the upper and lower tooth-like detent blocks, ensuring effective vertical and horizontal locking with each other, and preventing accidental openings of the fixture device 3.

Figure 18A:
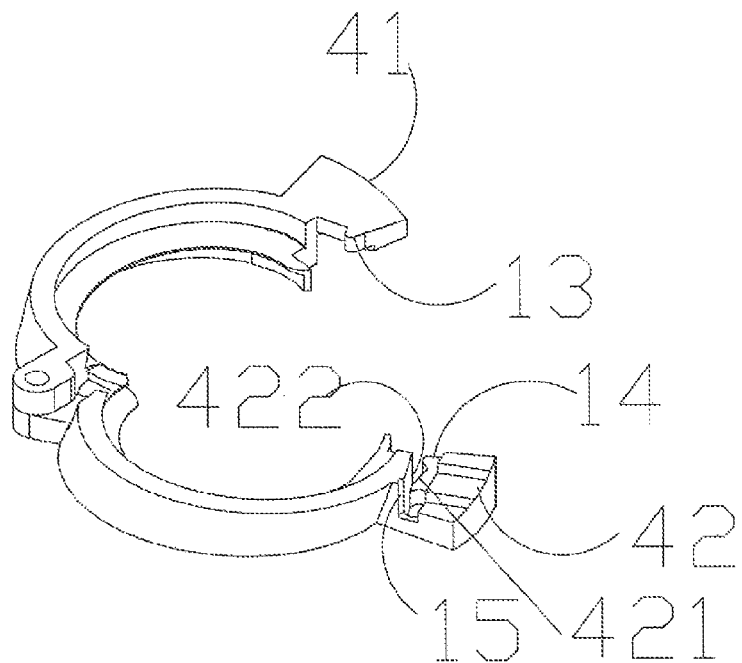
FIGS. 18A, 18B, 18C, and 18D are illustrations of various embodiments of the apparatus for circumcising a penis in an elliptical and oblique shape, comprising a hook and a linear groove.
Figure 18B:
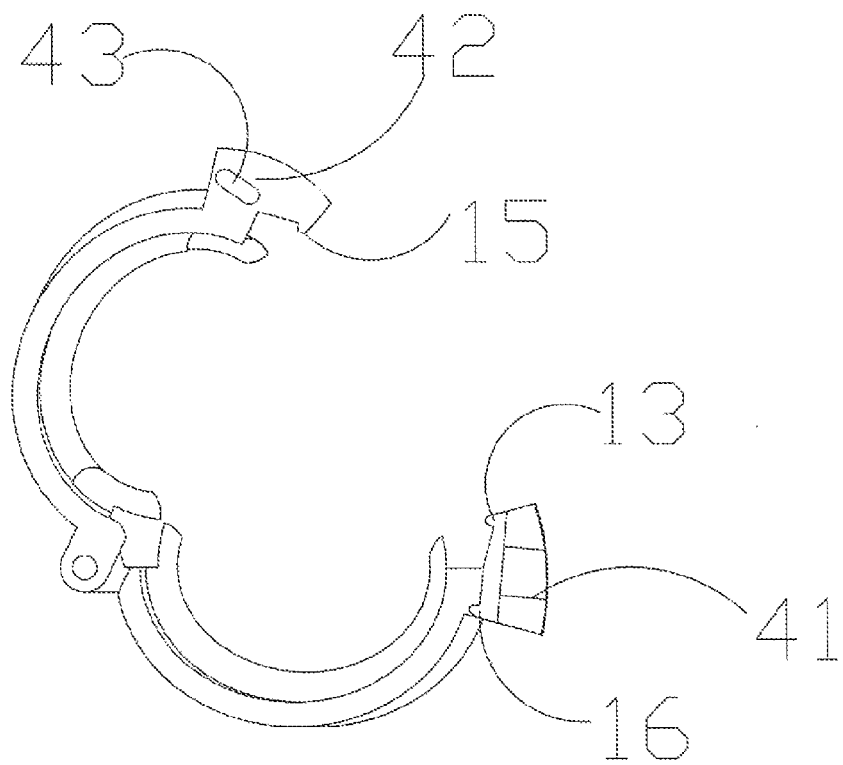
Figure 18C:
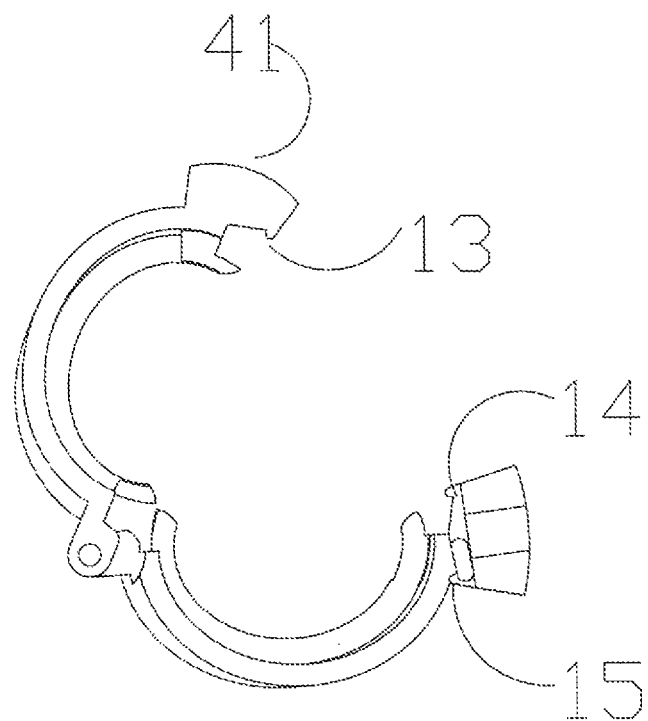
Figure 18D:
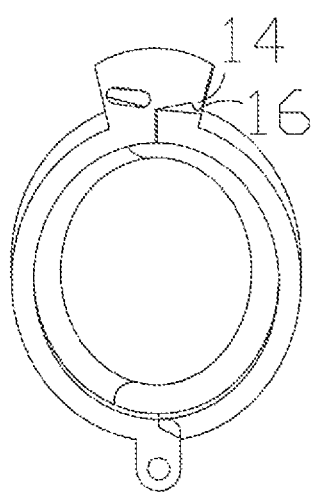

As shown in FIG. 18B, an unlocking hole 43 may be provided on the lower scalariform detent block 42 or on the upper scalariform detent block 41. When a circumcision procedure has been completed, a special tool may be inserted into the unlocking linear groove 43, thereby prying the detent blocks from one another and allowing removal of the circumcision apparatus.

Figure 19A:
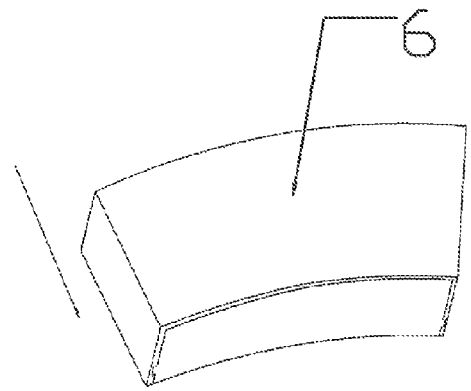
FIGS. 19A, 19B, 19C, 19D, and 19E illustrate a protective cover used in conjunction with the fixture device, with FIG. 19A illustrating a perspective view of the protective cover body, FIG. 19B illustrating a bottom view of the protective cover body, FIG. 19C illustrating a cut-away view of the interior of the protective cover body, FIG. 19D illustrating a side view of a protective cover cap used to seal the protective cover body, and FIG. 19E illustrating a bottom view of the protective cover cap.
Figure 19B:
Figure 19D:
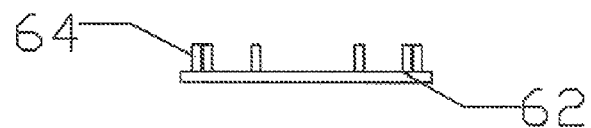
Figure 19C:
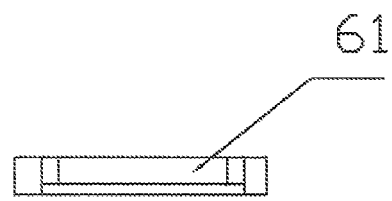
Figure 19E:
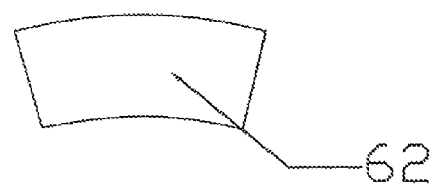

FIGS. 19A and 19E illustrate a protective cover 6 that may be placed onto the buckling device to prevent accidental opening of the fixture device 3 after surgery. The protective cover 6 comprises a cover body having a bottom plate, two side walls and a top wall (FIG. 19C). Cap 62 substantially matches the bottom plate so that protective cover 6 forms a cavity 61 that substantially matches the contour of the buckling device when cap 62 is placed on top of the cover body. The cap 62 is secured to the cover body typically using one or more fastening devices, such as screws, bolts, Velcro, etc., or using one or more rods 64 attached to cap 62, as shown in FIG. 19D, that may be snugly inserted into corresponding linear grooves 63 formed on the cover body rim. The protective cover may be constructed of, in one embodiment, resilient silica-gel for convenient use. The protective cover can effectively minimize the risk of accidental openings of the fixture device after surgery, which may result from an erection of the penis, thereby increasing the likelihood of a successful operation.

Figure 20A:
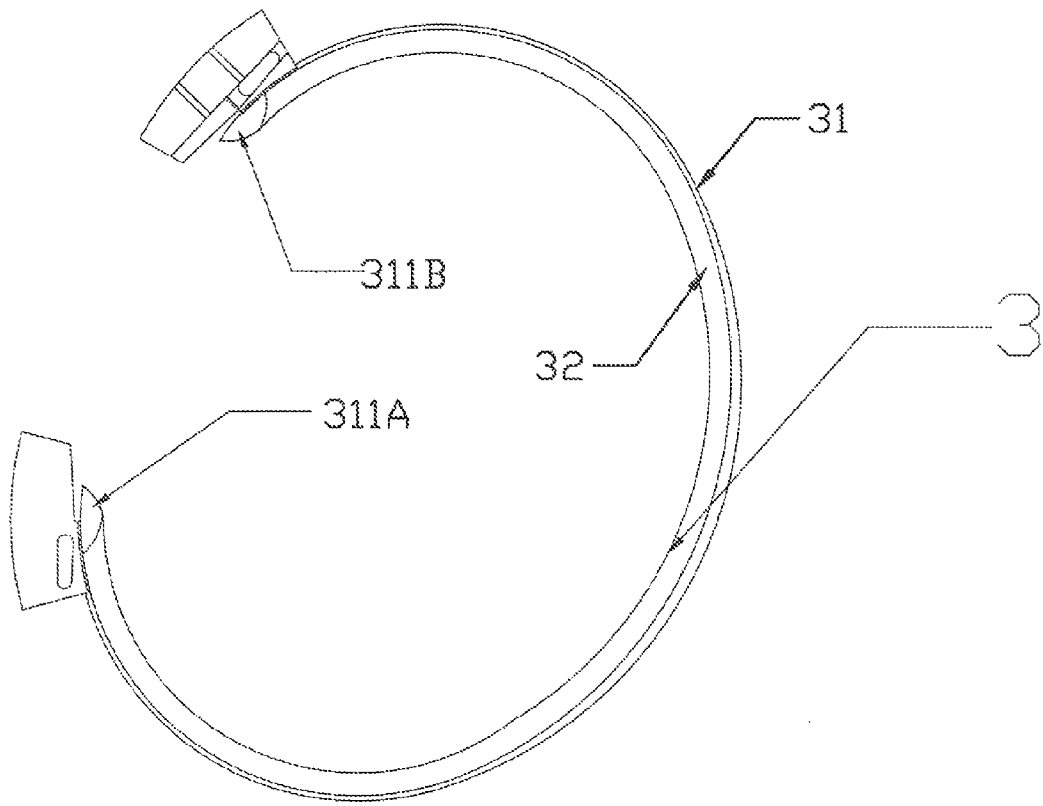
FIGS. 20A and 20B illustrate an embodiment of a fixture device shown as a flexible, C-shaped structure.
Figure 20B:
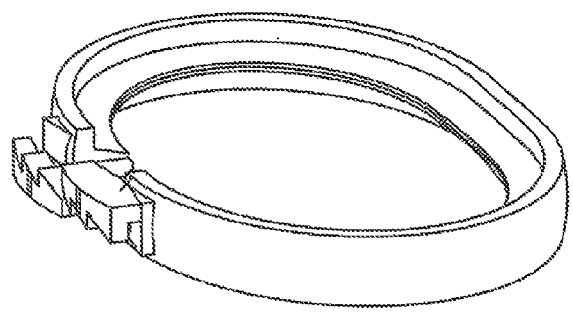

FIG. 20 illustrates another embodiment of the fixture device shown in FIG. 1A, as fixture device 30. Fixture device 30 comprises a C-shaped ring that is made of soft materials that may enable it to open wider when needed.

Figure 21A:
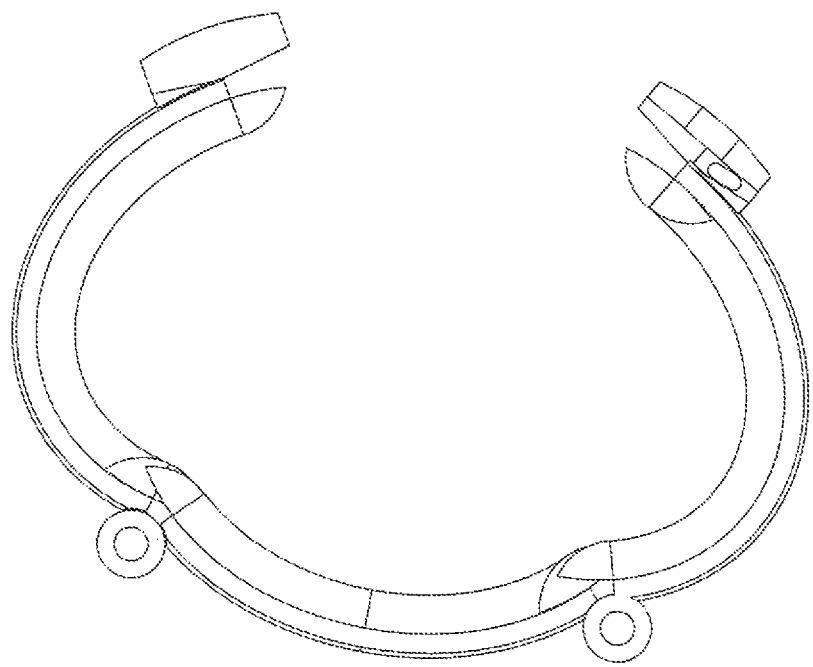
FIGS. 21A and 21B illustrate an embodiment of a fixture device comprising three sections.
Figure 21B:
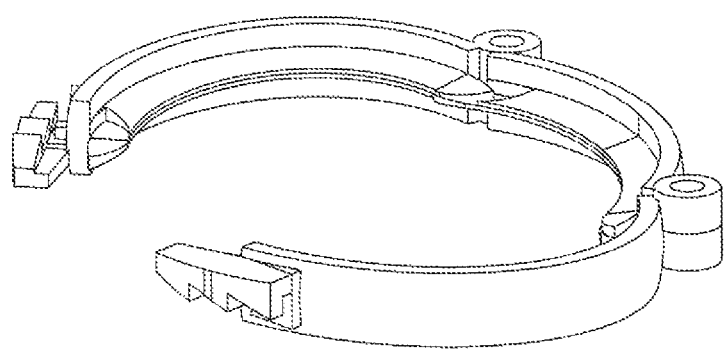

FIGS. 21A and 21B illustrate an embodiment where the fixture device comprises three sections. As mentioned above, in the two-section design, the hinge 35 is usually situated on the scrotum during surgery, typically causing friction between the hinge and the scrotum. The three-section design effectively eliminates the single hinge 35 from the center of the circumcision apparatus and replaces it with the two hinges shown in FIGS. 21A and 21B. Thus, the placement of the two hinges allow the scrotum to be placed therebetween, thereby reducing friction with the scrotum.

I claim:

1. A disposable circumcision apparatus, comprising:
   a fixture device comprising a surrounding wall, the surrounding wall comprising an opening;
   at least one blade layer protruding from an interior surface of the surrounding wall;
   a cushion ring; and
   a balanus ferrule for placement within the cushion ring;
   wherein:
   each of the at least one blade layer extends from a first end to a second end, the first end is located on the interior surface of the surrounding wall, the second end is spaced from the interior surface of the surrounding wall;
   the second end further includes a blade interior circumferential edge,
   the surrounding wall extends upwardly and downwardly along a height of the surrounding wall, the height of the surrounding wall is greater than the thickness of the first end such that the surrounding wall extends above and below the first end;
   a groove is formed along the blade interior circumferential edge to receive the cushion ring.

2. The apparatus of claim 1, wherein:
   the cushion ring is made of silica-gel and the at least one blade layer is made of plastic, and the cushion ring adheres to the at least one blade layer through an integral formation between plastics and silica-gel.

3. The apparatus of claim 2, wherein:
   the fixture device is coated with a silica-gel layer, and the silica-gel layer adheres to the fixture device through an integral formation between plastics and silica-gel.

4. The apparatus of claim 1, further comprising:
   a circular elastic pad, wherein the elastic pad is placed around an exterior of the balanus ferrule.

5. The apparatus of claim 4, wherein the balanus ferrule further comprises:
   a first rim located on a first side of the balanus ferrule; and
   a second rim located on a second side of the balanus ferrule; wherein
   the first and second rims form a ring-shaped cavity upon which the elastic pad rests.

6. The apparatus of claim 4, wherein the cushion ring and the elastic pad comprises a micro mechanism for preventing skin adhesion to the cushion ring and the elastic pad.

7. The apparatus of claim 6, wherein:
   the micro mechanism is selected from the group consisting of sinking and bulging dots, crossed sinking and bulging lines, grooves, protrusions, and an uneven structure.

8. The apparatus of claim 1, wherein:
   the fixture device and the balanus ferrule comprise an elliptic or obliquely elliptic structure corresponding to a cross section of a coronal sulcus.

9. The apparatus of claim 1, wherein the balanus ferrule further comprises a notch for accommodating a frenulum of prepuce.

10. The apparatus of claim 1, wherein:
    the fixture device is C-shaped.

11. An apparatus as claimed in claim 1, wherein:
    the fixture device comprises three sections connected together at two hinge points, the hinge points staggered from each other so that they minimize contact with a scrotum during circumcision surgery.

12. The apparatus of claim 1, furthering comprising a mechanism for maintaining the fixture device in a closed position, wherein the mechanism includes an upper scalar form detent block and a lower scalar form detent block, each scalar form detent block includes a hook and a hole, and the hook is sized and shaped to fit within the hole.

13. The apparatus of claim 12, further comprising a protective cover, sized and shaped to fit over the mechanism for maintaining the fixture device in the closed position.

14. The apparatus of claim 1,
    furthering comprising a mechanism for maintaining the fixture device in a closed position, wherein the mechanism includes a screw on one end of the fixture device and a linear threaded hole on the other end of the fixture device.

15. The apparatus of claim 1, wherein:
    the at least one blade layer comprises one blade layer, two blade layers, or three blade layers.

16. The apparatus of claim 1, wherein each of the least one blade layer comprises at least two thinner portions matching with and accommodating each other, the two thinner portions are provided with round angles.

17. The apparatus of claim 1, wherein the thickness of the second end is less than the thickness of the first end.

18. The apparatus of claim 1, wherein the cross-section of the groove is selected from a group consisting of an arc, a semi-circle, a semi-ellipse, and a triangle; and
    the cushion ring comprising a cross section substantially matching the cross section of the groove.

* * * * *